United States Patent [19]

Pepe et al.

[11] 4,046,794
[45] Sept. 6, 1977

[54] UREA SILICON PRODUCT AND USES THEREOF

[75] Inventors: Enrico J. Pepe; James G. Marsden, both of Amawalk, N.Y.

[73] Assignee: Union Carbide Corporation, New York, N.Y.

[21] Appl. No.: 370,849

[22] Filed: June 18, 1973

Related U.S. Application Data

[60] Division of Ser. No. 244,280, April 14, 1972, Pat. No. 3,754,971, which is a division of Ser. No. 759,524, Sept. 12, 1968, Pat. No. 3,671,562, which is a continuation-in-part of Ser. No. 729,895, May 17, 1968, abandoned.

[51] Int. Cl.² .......................... C07F 7/10; C07F 7/18
[52] U.S. Cl. ...................... 260/448.2 N; 260/448.2 E; 260/448.8 R; 260/46.5 E
[58] Field of Search ................ 260/448.8 R, 448.2 N, 260/448.2 E, 347, 46.5 E

[56] References Cited

U.S. PATENT DOCUMENTS

| 2,907,782 | 10/1959 | Pike | 260/448.8 R X |
| 3,361,783 | 1/1968 | Fink | 260/448.2 N |
| 3,506,701 | 4/1970 | DiPaola | 260/448.2 N |
| 3,671,562 | 6/1972 | Pepe et al. | 260/448.8 R |
| 3,726,907 | 4/1973 | Tesoro et al. | 260/448.8 R |

OTHER PUBLICATIONS

Rochow, "Chemistry of the Silicones", John Wiley and Sons, Inc., N.Y. (1946), p. 35.

*Primary Examiner*—Paul F. Shaver
*Attorney, Agent, or Firm*—George A. Skoler

[57] ABSTRACT

This invention relates to urea containing silicon compounds

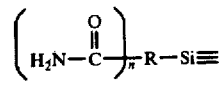

and the uses thereof, particularly as coupling agents on glass and to the similar use of substituted urea containing silicon compounds.

3 Claims, No Drawings

UREA SILICON PRODUCT AND USES THEREOF

This application is a division of copending application Ser. No. 244,280 filed Apr. 14, 1972, now U.S. Pat. No. 3,754,971, which in turn is a division of application Ser. No. 759,524 filed Sept. 12, 1968, now U.S. Pat. No. 3,671,562 issued June 20, 1972, which last application is a continuaion-in-part of abandoned application Ser. No. 729,895 filed May 17, 1968.

This invention relates to new urea substituted silicon-containing compositions of matter, processes for producing them, and their uses; as well as new uses for a variety of other urea substituted silicon-containing compounds.

One embodiment of this invention relates to new silicon compounds characterized by the presence of the following radical:

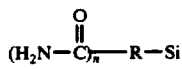

wherein at least one of the three free valences of the silicon atom are bonded directly to hydrolyzable groups such as alkoxy, acyloxy, aryloxy, amino, and the like, and/or oxygen which in turn is bonded to other silicon atoms to form a siloxane. The remaining free valences of the silicon atom are bonded by carbon to silicon bonds to monovalent organic groups. In the above formula I, R is an alkylene radical containing at least 3 carbon atoms and at least 1 nitrogen atom therein bonded to each (H$_2$NCO—+ to form (H$_2$HCON<); at least one free valence of (H$_2$NCON<) is bonded to an alkylene carbon atom of R, any other free valences thereof are bonded to either hydrogen, alkyl, aryl, cycloalkyl, aralkyl, and the like; any nitrogen in R is separated from silicon by at least three sequential carbon atoms; and n is at least 1 and typically not greater than about 3.

Specifically illustrative of such urea substituted silicon compounds are those depicted by the following formula:

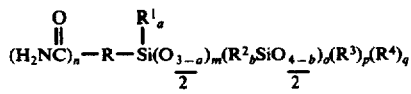

wherein R and n are described above, R$^1$ is any monovalent organic group bonded to silicon by a carbon to silicon bond and typically contains not more than about 12 carbon atoms; R$^2$ can be hydrogen and/or R$^1$; R$^3$ is a hydrolyzable and/or condensable radical such as hydroxyl, alkoxy, aryloxy, acyloxy and the like; R$^4$ is hydrogen, alkyl aryl, acyl and the like; m is 0 or 1; a is 0, 1 or 2; b is 0, 1, 2, or 3; o is 0 or 1; p is equal to 3-a when m is 0, and when m is 1, p is 0; and q is 0 when p is equal to 3-a and q is 0 or a positive number when m is 1.

Illustrative of R$^1$ is any monovalent organic radical such as alkyl (e.g., methyl, ethyl, pentyl, dodecyl, octadecyl, 2-ethylhexyl, and the like), cycloalkyl (such as cyclobutyl, cyclohexyl, 4-methylcyclohexyl, and the like), aryl (such as phenyl, 2-naphthyl, 2-anthracyl, biphenyl, and the like), alkaryl (such as 4-methylphenyl, 2,4-diethylphenyl, 4-dodecylphenyl, and the like), aralkyl (such as phenylethyl), alkenyl (such as vinyl, allyl, 3-butenyl, oleyl, and the like), alkadienyl (such as 1-butdienyl-1,4, 1-octadecatrienyl-9, 11, 13-, 1-neoprenyl, and the like), cycloalkenyl (such as 3-cyclohexeyl), haloalkyl (such as chloromethyl, gamma-chloropropyl, 3,3,3-trifluoropropyl, perfluoropropyl, haloaryl (such as 4-chlorophenyl, 2,4-dichlorophenyl, chloronaphthyl), halocycloalkyl (such as 4-chlorocyclohexyl), cyanoalkyl (such as beta-cyanoethyl, gamma-carboxypropyl and the like); cyanoaryl (such as 4-cyanophenyl); cyanocycloalkyl (such as 4-cyanocyclohexyl, 3-cyanocyclopentyl, and the like); carboxyalkyl (such as beta-carboxyethyl, gamma-carboxypropyl, and the like); carboxyaryl (such as 4-carboxyphenyl); carboxycycloalkyl (such as 4-carboxycyclohexyl, 3-carboxycyclopentyl, and the like; isocyanatoalkyl (such as gamma-icocyanatopropyl, delta-isocyanatobutyl, and the like); isocyanatoaryl (such as 4-isocyanatophenyl); isocyanatocycloalkyl (such as 4-isocyanatocyclohexyl); alkyl or aryl carboxyalkyl (such as betamethylcarboxyethyl, gamma-phenyl carboxypropyl, and the like); hydroxyalkyl (such as hydroxymethyl, gamma-hydroxypropyl, and the like); hydroxy(polyalkyleneoxy)alkyl (such as omega-hydroxy(polyethyleneoxy)propyl, and the like); alkenoyloxyalkyl (such as gamma-acrylyloxypropyl, gamma-methacryloxypropyl, and the like); epoxyalkyl (such as 1,2-epoxyethyl, 1,2-epoxypropyl, 1,2-epoxybutyl, and the like); epoxy alkyloxyalkyl (such as glycidyloxypropyl); epoxycycloalkyl (such as beta-3,4-epoxycyclohexylethyl); aminoaryl and aminoalkyl (such as aminomethyl, gamma-aminopropyl, delta-aminobutyl, p-aminophenyl, and the like); and the like.

Illustrative of alkoxy, acyloxy, aryloxy, amino, and the like, such as mentioned above and characterized by R$^3$ or R$^4$ when q is a positive number, are for example methoxy, ethoxy, propoxy, dodecyloxy, isopropoxy, and the like; phenoxy, naphthyloxy, biphenyloxy, and the like, alkylamino and arylamino (such as methylamino, diethylamino, phenylamino, and the like), formyloxy, acetyloxy, proprioxy, and the like, any organo-functional radicals such as hydroxyalkoxy (such as beta-hydroxyethoxy, gamma-hydroxypropoxy, and the like); hydroxyalkoxyalkoxy (such as beta-hydroxyethoxy-ethoxy, omega-hydroxy(polyethyleneoxy)ethoxy, omega-hydroxy (poly-1,2-propyleneoxy), and the like; cyanoalkoxy (such as beta-cyanoethoxy, beta-cyanohexoxy and the like); cyanoalkoxy-alkoxy (such as beta-cyanoethoxyethoxy, omega-cyanoethoxy(polyethyleneoxy), omega-cyanoethoxy(poly-1,2-propyleneoxy), and the like); carboalkoxy (such as beta-carboxyethoxy, beta-carboxyhexoxy and the like); haloalkoxy (such as chloromethoxy, bromoethoxy perfluoropropoxy, and the like); and the like.

The products of this invention may be produced by the treatment of silanes or siloxanes characterized by the following formula:

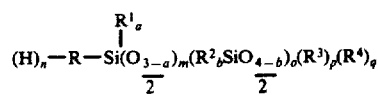

wherein the hydrogen which is present n times in formula III is bonded to the nitrogen referred to previously with respect to the definition of R; or

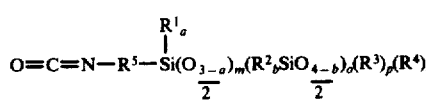

wherein R is a divalent alkylene radical of at least 3 carbon atoms and which separates the isocyanato group from silicon by at least three sequential carbon atoms; and R¹, R², R³, R⁴, n, m, a, b, o, p, and q are described above.

The treatment of the silanes or siloxanes characterized by formulae III and IV are different in order to make the ureas of formulae I and II. The amine of formula III is converted to urea by the reaction of the silanes or siloxanes of formula III with an organocarbamate such as alkyl, cycloalkyl or aryl carbamates illustrated by methyl carbamate, ethyl carbamate, and n-propyl carbamate, n-butyl carbamate, cyclohexylcarbamate phenyl carbamate, 4-methylphenyl carbamate, 4-dodecyl phenyl carbamate, biphenyl carbamate; and alkylene, cycloalkylene and arylene carbamates, such as ethylene dicarbamate, 1,4-butylene dicarbamate, 1,4-phenylene dicarbamate, 4,4'-bisphenylene dicarbamate, 1,4-cyclohexylene dicarbamate, and the like. The reaction can be carried out neat or in solution or dispersion using solvents or nonsolvents for the silane and/or the carbamate reactants. Types of solvents and nonsolvents include water, hydrocarbon solvents, ether solvents, amide solvents, ketone solvents and the like, such as mineral spirits, hexane, n-nonane, benzene, toluene, xylene, methylethyl ketone, methylisobutyl ketone, diethylether, di-n-diisopropyl ether, N,N-dimethyl formamide, and the like. The temperature of the reaction can be relatively low depending upon the reactivity of the carbamate and the amount of amine present in the reaction, usually temperatures in the range of about 40° to about 180° C. are satisfactory. Typically a temperature about 50° C. to about 150° C. is more desirable.

This reaction can be operated under atmospheric or subatmospheric pressures. Superatmospheric pressures are employable but are not considered to operate as beneficially as subatmospheric and atmospheric pressures. The reaction product can be separated by distillation, crystallization, decantation, and the like, utilizing standard processing equipment and procedures.

The treatment of an isocyanato silicon compounds of formula IV to produce the urea involves the reaction of ammonia with the isocyanate. This reaction can proceed at exceedingly low temperatures, viz., as low as −75° C., or lower, typically at least −50° C., and usually not greater than about 150° 1 C. The reaction also can be performed neat or in admixture either by dissolution or suspension of either one or both of the reactants in a solvent or nonsolvent, as the case may be. Usually, the isocyanate of formula IV is liquid, most desirably in solution, and the ammonia is bubbled through the solution as a gas or is employed in liquid form. In the preferred process, the isocyanate is reacted with liquid ammonia. This minimizes the use of superatmospheric pressure as is required when using gaseous ammonia.

This invention also contemplates a number of other embodiments, particularly the utilities of the aforementioned ureas as well as ureas characterized by the following formula:

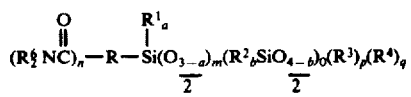

V wherein R, R¹, R², R³, R⁴, n, a, b, m, o, p, and q, are described above, and R⁶ may be alkyl or aryl, such as described above, provided at least one R⁶ is hydrogen or methylol, or both R⁶'s may be methylol, i.e., (—CH- ₂OH). These materials may be formed by reacting the product of formula II with an alkyl or aryl halide to add one alkyl or aryl group or by reacting aryl or alkyl amines with the isocyanate of formula IV or by reacting N-alkyl or N-aryl carbamate esters with the amine of formula III. The methylol substituted ureas may be formed by simple dissolution or dispersion of silanes or siloxanes characterized by formula II in aqueous formaldehyde solution, or by direct reaction of formaldehyde or its precursors, to wit, hexamethylenetetraamine or trioxane in a non-aqueous solvent solution of the silane or siloxane. Conventional art recognized reaction conditions may be employed.

The amines which may be treated in accordance with the process of this invention are those which are described in U.S. Pat. No. 2,971,864, patented Feb. 14, 1961, specific embodiments being illustrated in examples 1, 2, 3, 4 and 6 thereof; U.S. Pat. No. 2,832,754, particularly at Examples 1, 2, 3 and 4 thereof; U.S. Pat. No. 2,942,019 at columns 1, 2, 3 to lines 17 of column 4 with respect to silanes and siloxane homopolymers and copolymers which are described therein to be reacted with aldehydes and ketones.

It has be found that the above ureas, used as aqueous solutions of the hydrolyzates of the aforedescribed urea substituted silanes of formulas II and V, or the partially condensed to totally condensed siloxanes of formulas II and V employed neat or in solution, can be most effective coupling agents, particularly on fiber glass for further reaction with a broad variety of thermosetting and/or thermoplastic resins. They can be added first onto the glass followed by treatment with the resin or they can be premixed with the resin and added to glass. In any event, it is found that these silanes and siloxanes supplied to the glass surface to form a siloxane coated thereon act to strongly adhere resin either simultaneously or thereafter supplied to the glass. Illustrative of resins which can be effectively bonded include the thermosetting resins, such as the phenol formaldehyde, melamine-formaldehyde, polyester resins, such as those formed by the reaction of ethylene glycol, maleic acid or anhydride with or without styrene monomer and/or polymer, alkyd resins, polyurethane resins, epoxy resins, and the like. It may also be used to couple thermoplastic resins which possess reactive groups, such as isocyanate, carboxy, epoxy, and the like, by the inclusion in the resin of a catalyst for enhancing the reaction such as the well known metal catalysts, e.g., tin octoates, alkyl tin compounds, lead, cobalt, manganese, zinc, titanate and the like, driers and catalysts to enhance the reaction to the urea siloxane with the resin on the glass fiber surface. Also there may be included in the resins peroxide and hydroperoxide catalysts for the resins to achieve theoretical formation of fragments from the urea siloxanes on the glass surface which add to the resin and vice versus. Resins which most suitably respond to this type of reaction system include the thermoplastics, such as polyethylene, polypropylene, copolymers of ethylene and propene, polyvinylchloride, polyvinylbutyral, polyacrylonitrile, copolymers of styrene and acrylonitrile, copolymers of styrene and butadiene-1,3, copolymers of acrylonitrile and vinylchloride, and the like. The invention is particularly useful in this area in enhancing the bonding of polyvinylbutyral resin to plate glass in the manufacture of plate glass laminates. The urea substituted siloxanes also act as effective coupling agents on other inorganic substrates such as siliceous pigments and fillers, e.g., clay, silica, hydrated silica, fumed silica, sand and the like. The silanes are most effectively employed in treating sand which can be employed in foundry molding using hot or cold curing resins of the phenol-formaldehyde, resorcinol-formaldehyde, and melamine-formaldehyde type. These ureas substituted siloxanes enhance the bonding of the resin to the sand.

EXAMPLE 1 a. Ammonia method

Into a 1-liter, 3-necked flask fitted with dry-ice condenser, thermometer, magnetic stirrer and dropping funnel is charged about 100 ml. of liquid ammonia. Over a period of 30 minutes, 205.3 grams (1.0 moles) of γ—OCN(CH$_2$)$_3$Si(O Me)$_3$ is added, dropwise with stirring. External cooling with a dry-ice and acetone bath is used to maintain a reaction temperature of −30° to −40° C. The excess ammonia is removed by sparging with dry nitrogen over a period of 1 hour. A vacuum strip to 80° C./10 mm. produces the clear, colorless and somewhat viscous urea derivative,

in near quantitative yields.

Infrared spectral survey is in agreement with the assigned monosubstituted urea structure, calc for C$_7$H$_{18}$SiO$_4$N$_2$— 37.8% C; 8.2% H; 12.6% Si; 12.6% N; 41.9%, OMe. Anal. — 38.1, 8.1, 12.7, 12.2, 39.6.

b. Transesterification method

Into a 500 ml. distillation flask outfitted with thermometer and attached to a 1 foot distillation Vigreaux column, distillation head and receiver is charged 110.5 gms. (0.5 moles) of γ—NH$_2$ (CH$_2$)$_3$Si(O Et)$_3$, 44.5 gms. (0.5 moles) of

and 250 ml. of toluene. Titration of the total mixture in isopropyl alcohol, using standardized 0.1N HCl and brom cresol green indicator, shows the presence of 1.17 meg. of —NH$_2$ per ml. The reaction mixture is heated to reflux at 130° C. while removing 5 ml. of distillate boiling at from 105° to 110° C. at atmospheric pressure over 1 hour. Retitration of the total reaction mixture indicates 1.64 meg/ml. of —NH$_2$. At this point, 0.5 gms. of dibutyl-tin oxide is added and reflux continues for 3 hours during which time 186 gms of a 83% toluene — 15.1% EtOH(ethanol) mixture is removed at the head, boiling at from 105° to 110° C. at atmospheric pressure. Removal of the balance of toluene and ethanol by vacuum stripping to 100° C. at 1 mm. mercury pressure produces 138.4 gms. (104 weight % of calculated yield) of crude

containing 0.03 meg/ml. of residue —NH$_2$ (94 mole % conversion). Infrared spectral survey verifies the presence of monosubstituted urea structure. Aside from the expected differences due to triethoxysilicon groups, the major absorption characteristics are identical to those obtained from the product of Example 1a.

EXAMPLE 2

Composites were prepared as follows:

500 grams of glass beads range in sizes from 325 to 40 mesh, U.S. Standard, are mixed with 30.9 grams of a 50 percent aqueous solution of methylol rich A-stage phenol-formaldehyde resin (approximately 3 weight percent resin solids based on weight of glass beads), 0.9 gram of concentrated aqueous NH$_4$OH solution, 7.7 grams of water and 0.016 grams of silane (0.1 weight percent silane based on resin solids). This mixture is placed in a multiple cavity dumbbell shaped mold and cured for 7 min. at 450° F. to produce a cured article of the mold shape.

The following table shows tensile strengths of a number of such molded articles, the differences between each being the use of silane as set forth in the table:

| Silane | Tensile Strength Results | |
|---|---|---|
| | Dry | 16 hrs. in H$_2$O at 50° C. |
| Control (No Silane) | 265 | 0 |
| NH$_2$CH$_2$CH$_2$N(H)(CH$_2$)$_3$Si(OCH$_3$)$_3$ | 387 | 110 |
| (CH$_3$O)$_3$Si(CH$_2$)$_3$N(H)—C(=O)—N(H)(CH$_2$)$_3$Si(OCH$_3$)$_3$ [1] | 392 | 115 |
| CH$_3$N(H)—C(=O)—N(H)(CH$_2$)$_3$Si(OCH$_3$)$_3$ [2] | 372 | 173 |
| CH$_3$—CH(CH$_3$)—C(=O)—N(H)(CH$_2$)$_3$Si(OCH$_3$)$_3$ [3] | 323 | 86 |
| NH$_2$—C(=O)—N(H)(CH$_2$)$_3$Si(OCH$_3$)$_3$ | 458 | 298 |

[1]Produced according to the following reaction:

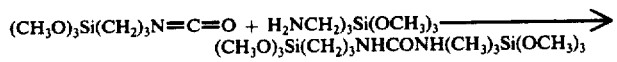

[2]Produced according to the following reaction:

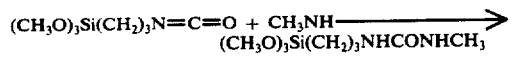

[3]Produced according to the following reaction:

| | Tensile Strength Results | |
|---|---|---|
| Silane | Dry | 16 hrs. in H₂O at 50° C. |

EXAMPLE 3

Into a 3-liter, 3-necked flask outfitted with thermometer, heating mantle, mechanical stirrer and a 12 inch Vigreaux column with distillation head and receiver is charged 1,100 gms. (5.0 moles) of NH₂(CH₂)₂NH(CH₂)₃Si(OMe)₃, 375 gms. (5.0 moles) of methyl urethane, MeOOCNH₂, 908 gms. of anhydrous toluene and 3.9 gms. (0.25 wgt %) of dibutyl tin oxide. The stirred mixture is heated at reflux from 96° to 119° C for 5 hours, during which time 751.9 gms. of distillate is removed boiling at from 64° to 109° C at atmospheric pressure and determined by gas chromatographic analysis to contain approximately 24 volume % methanol and 76 volume % toluene. Exactly one half of the total reaction mixture is removed and stripped under vacuum to 100° C at 1 mm. of mercury pressure to produce 605 gms. (2.28 moles) of

EXAMPLE 4

To 605 grams (2.28 moles) of

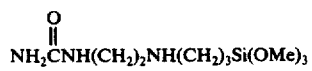

dissolved in 1400 gms. of toluene is added an additional 187.5 gms. (2.5 moles) of methyl urethane and the procedure described above is repeated to produce 668 gms. (2.17 moles) of light yellow, high viscosity

in 95.4 mole % yield.

EXAMPLE 5

In much the same manner as described in Example 3, 590 gms. (6.0 moles) of NH₂(CH₂)₂NH(CH₂)₂NH(CH₂)₃Si(OMe)₃ is reacted with 450 gms. (6.0 moles) of MeOOCNH₂ until 6 moles of by-product methanol has been formed and removed by distillation. One third of the total reaction mixture is removed and vacuum stripped to 100° C/1.0 mm. to obtain 615.6 gms. (2.0 moles) of the mono-urea derivative,

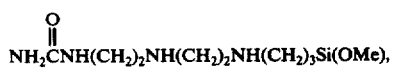

a light yellow viscous syrup soluble in water, alcohols and toluene.

EXAMPLE 6

To the remaining 4 moles of mono-urea derivative obtained in Example 5 is added 300 gms., 4.0 moles of additional MeOOCNH₂, 1 liter of toluene and the process of methanol removal described above repeated until an additional 4 moles of methanol is formed and removed. The crude reaction mixture is divided in half and isolation of the di-urea derivative accomplished as described above. There results 643 gms. (1.83 moles) of thermoplastic light orange, glass-like (at room temperature, 25° C.) di-urea derivative.

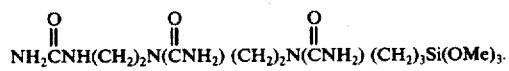

which is soluble in methanol, ethanol, isopropanol, water and toluene.

EXAMPLE 7

To the remaining di-urea derivative prepared in Example 6 is added 150 gms. (2.0 moles) of MeOOCNH₂, 500 ml of additional toluene and the transesterification reaction driven to completion in the same manner as described above. The results upon workup in the aforementioned manner a quantitative yield of the tri-urea derivative, NH₂CNH(CH₂)₂N(CNH₂) (CH₂)₂N(CNH₂) (CH₂)₃Si(OMe)₃.

The latter is amine free, thermoplastic, clear orange, glass-like at room temperature and softens and flows at about 80° C. and is soluble in alcohols (e.g. methanol, ethanol, etc.) and water.

As noted above, the urea silanes are extremely effective coupling agents and are notably useful in coupling or enhancing the bonding of fiber glass to a plurality of organic materials such as rubber, e.g., ethylene-propylene terpolymer rubbers and butadiene-styrene rubbers. These silane coupling agents offer exceptional promise as coupling agents in making fiber glass reinforced rubber tires and other rubber goods.

"Me", as employed herein, means the methyl radical.

What is claimed is:

1. The hydrolyzate of:

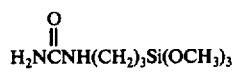

2. The hydrolyzate of:

3. The process of producing urea substituted silicon compounds which comprises reacting ammonia with the isocyanato groups of an isocyanatoorganosilicon compound having the formula:

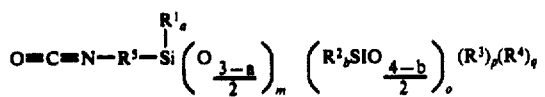

wherein $R^5$ is a divalent alkylene radical of at least 3 carbon atoms and which separates the isocyanato group from silicon by at least three sequential carbon atoms; $R^1$ is a monovalent organic grop bonded to silicon by a carbon to silicon bond, selected from the group consisting of alkyl, cycloalkyl, aryl, alkaryl, aralkyl, alkenyl, alkadienyl, cycloalkenyl, haloalkyl, halocycloalkyl, cyanoalkyl, cyanoaryl, cyanocycloalkyl, carboxyalkyl, carboxyaryl, carboxycycloalkyl, isocyanatoaryl, isocyanatocycloalkyl, alkyl, carboxyalky, aryl carboxyalkyl, hydroxyalkyl, hydroxy(polyalkyleneoxy)alkyl, alkenoxyloxyalkyl, epoxyalkyl, epoxy alkyloxyalkyl, aminoaryl and aminoalkyl; each $R^2$ is hydrogen or $R^1$; $R^3$ is a hydrolyzable or condensible radical, selected from the group consisting of hydroxyl, alkoxy, acyloxy, aryloxy, amino and haloalkoxy; $R^4$ is a member selected from the group consisting of hydrogen, alkyl, aryl and acyl; $m$ is 0 or 1; $a$ is 0, 1 or 2; $b$ is 0, 1, 2 or 3; $o$ is 1; $p$ is equal to 3-$a$ when $m$ is 0, and when $m$ is 1, $p$ is 0; and $q$ is 0 when $p$ is equal to 3-$a$ and $q$ is 0 or a positive number when $m$ is 1.

* * * * *